United States Patent [19]

Mori

[11] Patent Number: 4,727,029
[45] Date of Patent: Feb. 23, 1988

[54] APPARATUS AND METHOD FOR THE PRETREATMENT OF BIOLOGICAL SPECIMENS FOR USE IN SCANNING ELECTRON MICROSCOPES

[75] Inventor: Kintaro Mori, Katsuta, Japan

[73] Assignee: Hitachi Koki Company, Limited, Japan

[21] Appl. No.: 598,511

[22] Filed: Apr. 10, 1984

[51] Int. Cl.$^4$ .................. C12N 13/00; G01N 1/00; G01N 33/48

[52] U.S. Cl. ...................... 435/173; 424/3; 250/307

[58] Field of Search ............... 435/173, 287, 313, 29; 424/3; 204/165; 250/307

[56] References Cited

U.S. PATENT DOCUMENTS

| | | | |
|---|---|---|---|
| 3,775,058 | 11/1973 | Bush | 435/173 X |
| 3,775,308 | 11/1973 | Yasuda | 204/165 X |
| 3,876,373 | 4/1975 | Glyptis | 435/311 X |
| 3,962,057 | 6/1976 | Bartz | 204/165 X |
| 4,163,725 | 8/1979 | Sano et al. | 204/165 X |
| 4,265,276 | 5/1981 | Hatada et al. | 204/165 X |
| 4,447,374 | 5/1984 | Tanaka | 204/165 X |

FOREIGN PATENT DOCUMENTS 2950454  7/1981  Fed. Rep. of Germany.
WO80/00346  3/1980  PCT Int'l Appl. ............ 204/165

OTHER PUBLICATIONS

Optik 7, 1950, vol. 4/5, pp. 294–302.
Journal for Physics, vol. 129, 1951, pp. 491–503.
Vakuum Technik 1971, vol. 8, pp. 225–231.

Primary Examiner—Robert J. Warden
Assistant Examiner—Randall E. Deck
Attorney, Agent, or Firm—Lowe, Price, LeBlanc, Becker & Shur

[57] ABSTRACT

A method for pretreating a biological material for observation by scanning electron microscope which comprises: placing a biological material in a vacuum, supplying an inert gas to a predetermined level of pressure; and energizing the inert gas for ionization for a time sufficient to cause the surface of the biological material to be activated whereby when an electron beam is irradiated on the treated surfaces, secondary electrons are emitted in a high efficiency. The apparatus for carrying out the above method is also described.

3 Claims, 7 Drawing Figures

APPARATUS AND METHOD FOR THE PRETREATMENT OF BIOLOGICAL SPECIMENS FOR USE IN SCANNING ELECTRON MICROSCOPES

BACKGROUND OF THE INVENTION

1. Field of the Invention

This invention relates to the microscopic art and more particularly, to an apparatus and method for pretreating biological materials in the way suitable for observation by scanning electron microscopes.

2. Description of the Prior Art

As is well known, for observation of biological materials or specimens through scanning electron microscopes, primary electrons are irradiated on the surface of the specimen to generate secondary electrons therefrom having an energy below 100 eV and the thus generated secondary electrons are used as an information source of the image. However, because the biological specimen is an electrical insulator and tends to be electrically charged upon irradiation of the primary electrons, the resulting image may be defective and the secondary electrons may not be sufficiently emitted. This does not lead to high resolution for the material.

To avoid this, a biological specimen is coated, after fixation, dehydration and drying, by vacuum deposition with a metal such as gold onto the surface of the specimen. By this, emission of secondary electrons is ensured with the specimen being prevented from being electrically charged, thereby attaining high resolution. Where, however, a metal layer of several hundred angstroms in thickness is deposited on the specimen surface, it is difficult to observe fine portions of the specimen because of the presence of the metal layer. In addition, when gold or platinum is used for the vacuum deposition, the coating cost becomes high. With tungsten, the emissivity of secondary electrons is high with attendant high resolution but a problem is involved in that because of the high melting point of tungsten, a biological specimen which has poor resistance to heat tends to deteriorate by application of heat upon vacuum deposition.

SUMMARY OF THE INVENTION

It is accordingly an object of the invention to provide an apparatus and method for pretreating biological materials for observation by scanning electron microscopes which can solve the problems of the prior art.

It is another object of the invention to provide an apparatus and method for pretreating biological materials whereby even fine portions of the material are clearly observed by scanning electron microscopes.

It is a further object of the invention to provide an apparatus and method for pretreating biological materials in relatively simple and efficient manners for observation by scanning electron microscopes.

According to one embodiment of the invention, there is provided a method for pretreating a biological material for observation by scanning electron microscopes which comprises placing a biological material in a vacuum, supplying an inert gas to a predetermined level of pressure, and energizing the inert gas for ionization for a time sufficient to cause the surfaces of the biological material be activated by irradiation of the resulting ions on the surfaces of the biological material whereby when an electron beam is irradiated on the treated surfaces, secondary electrons are emitted in a high efficiency.

An apparatus for carrying out the above method is so constructed as to comprise a plasma discharge chamber having an inlet for an inert gas and an exhaust port and being capable of being maintained at a predetermined pressure, a means for evacuating the discharge chamber to a predetermined level of vacuum, and a means for energizing the inert gas being fed from the inlet for ionization of the inert gas so that a biological material set in the discharge chamber is irradiated on surfaces thereof with the ions until the surfaces of the biolgical material are activated. Preferably, the biological material is placed in a separate chamber which is connected with or communicates through a section having a plasma-inducing electrode therearound to the plasma discharge chamber. By this, even if the temperature within the discharge chamber is undesirably raised by energization of the inert gas, the material is not directly heated nor degraded in nature by the energized gas but is treated or activated with the plasma at a lower temperature.

DETAILED DESCRIPTION AND PREFERRED EMBODIMENTS OF THE INVENTION

Figure 1:
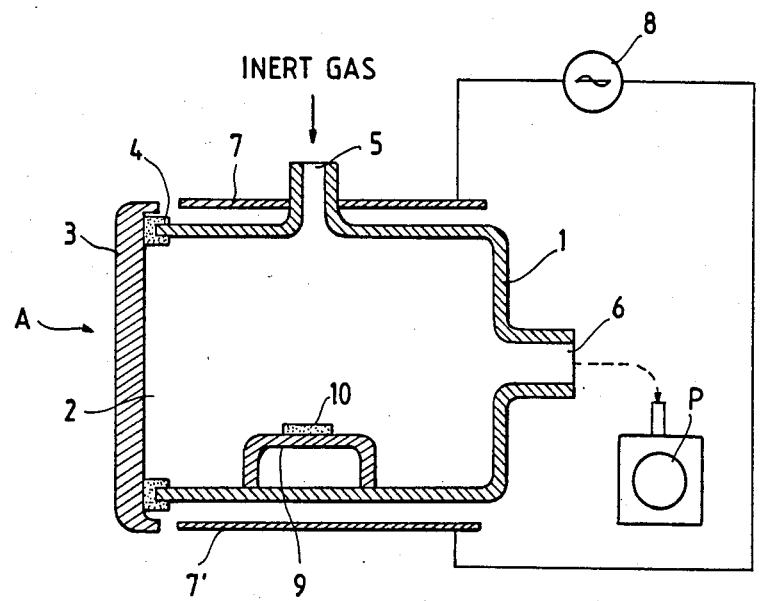
FIG. 1 is a schematic view, partially in section, of an apparatus for pretreating biological materials for observation by scanning electron microscopes according to one embodiment of the invention.

Reference is now made to the accompanying drawings in which like reference numerals identify like parts. In Fig. 1, there is generally shown a pretreating apparatus A which includes a discharge chamber 1 made of an insulating material such as glass and having a shape of a bottle lying on its side. The chamber 1 has an opening 2 and a cover 3 for the opening 2 made of a similar insulating material at one side thereof and a packing 4 such as of rubber ensuring hermetic sealing between the chamber 1 and the cover 3. The chamber 1 has also an inlet 5 through which an inert gas is charged thereinto from an inert gas source (not shown) and an exhaust port 6 connected to a vacuum pump P. A pair of capacitive electrodes 7 and 7' each, for example, in a semi-cylindrical form are placed to surround the bottle-shaped chamber 1 therewith and are connected with a high frequency power supply 8. The pair of capacitive electrodes are provided around the plasma discharge chamber in spaced and face-to-face relation. Within the chamber 1 is a specimen mount 9 having a biological specimen 10. The specimen is set in position through the opening 2 after removal of the cover 3.

In operation, the air in the chamber 1 is evacuated through the exhaust port 6 by means of the vacuum pump P so that the internal pressure of the chamber 1 is reduced to a level of 0.1 to 0.01 Torr. Subsequently, an inert gas such as argon, krypton, neon and the like is fed into the chamber 1 from the inlet 5 in an amount of from 10 ml/min to 150 ml/min so that the pressure within the chamber is maintained at 0.3–5 Torr. In this condition, a high frequency voltage from the power supply 8 is applied to the capacitive electrodes 7 and 7', so that the inert gas in the discharge chamber 1 is energized, causing the gas to be ionized, thereby forming a plasma. As a result, the specimen 10 in the chamber is hit or irradiated with the ions or dissociated inert gas in the plasma. The treatment is continued until the specimen suffers so-called "atomic fabrication" on the surface thereof, so that the specimen is activated on the surfaces thereof. The thus activated biological specimen is likely to emit secondary electrons when an electron beam is irradiated thereon. Even though the specimen is not vacuum deposited on the surface thereof with a metal, no electrical charging by application of primary electrons takes place on the specimen surfaces during observation by scanning electron microscopes. Satisfactory emittance of secondary electrodes permits a greatly magnified image similar to those attained by vacuum deposition of metal. In addition, because no metal layer of several hundred angstroms in thickness is deposited on a biological specimen, the specimen can be more finely observed.

Although the treating conditions may vary depending on the capacity of the discharge chamber, the type of biological specimen, the high frequency power and the like, a biological specimen may be treated within 5 minutes or more when high frequency power being applied is about 10 W and the discharge chamber is made of a glass tube having an inner diameter of about 80 mm. The rise of temperature within the discharge chamber at high frequency power of 10 W is about 20° C. Thus, the biological specimen suffers little damage thereon in many cases. In general, the high frequency output power used ranges from 5 to 20 W and the treating time ranges from 5 to 10 minutes.

Figure 2:
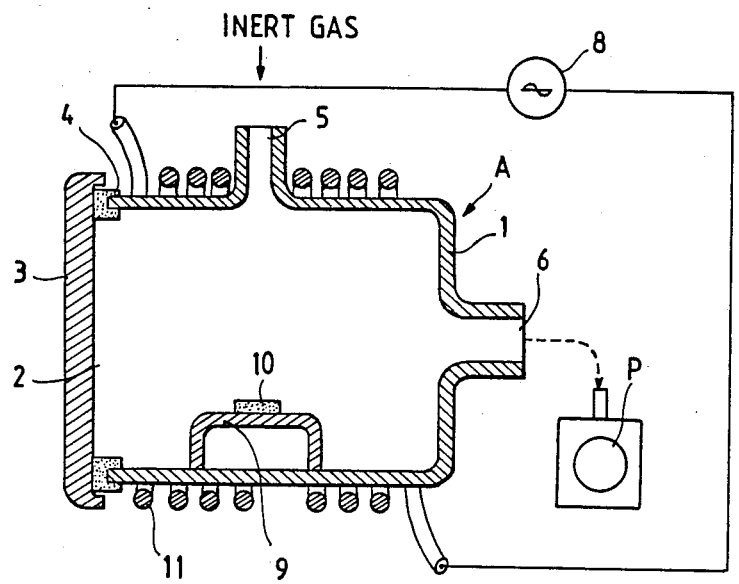
FIG. 2 is a view similar to FIG. 1 but shows another embodiment of the invention.

The apparatus shown in FIG. 2 is similar to the apparatus of FIG. 1 except that a pair of capacitive electrodes 7, 7' are replaced by an inductive coil electrode 11. In this case, similar results are attained.

As mentioned above, the temperature of the discharge chamber may more or less increase upon application of high frequency power to the inert gas for ionization. This increase may damage highly heat-sensitive biological specimens. In order to further improve the apparatus of the type described above, it is preferable that a biological specimen is placed in a chamber different from the discharge chamber by which the specimen is not directly heated by the discharge of an inert gas and the influence of heat generated by the energization is minimized. To this end, the ions generated by the discharge of an inert gas should be properly induced towards the chamber in which the specimen is placed. This is particularly described in FIGS. 3 and 4.

Figure 3:
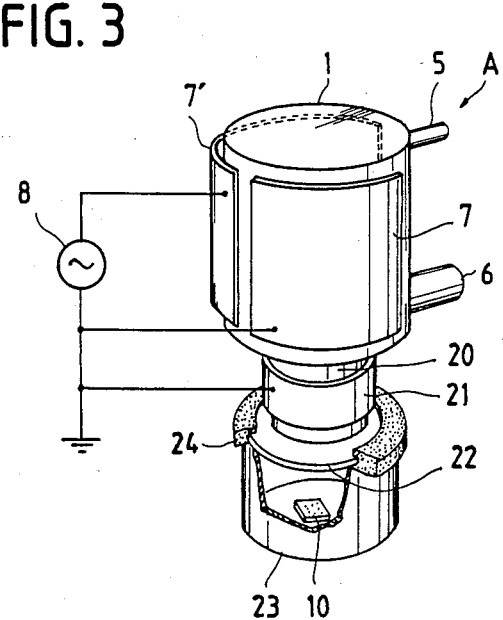
FIG. 3 is a perspective view showing a further embodiment of the invention.

In FIG. 3, there is shown the discharge chamber 1 which is similar in construction to those of FIGS. 1 and 2 except that the chamber 1 does not include the cover 3 with the packing 4 or the mount 9 for the specimen 10 and is designed to have the inlet 5 and the exhaust port 6 in a different manner. The chamber 1 has a pair of capacitive electrodes 7, 7' similar to the embodiment of FIG. 1. The chamber 1 is fixedly or integrally connected at the lower end thereof to a plasmainducing section or hollow cylinder 20 with an electrode ring 21 as shown. The hollow cylinder 20 is extended, preferably coaxially, from the chamber 1. The electrode ring 21 is connected to the high frequency power supply 8 at a ground side thereof. The hollow cylinder 20 has a flange 22 which is detachably attached to a treating chamber 23 for a biolgical specimen 10 through a rubber packing 24.

In operation, the specimen 10 is pretreated as follows. The specimen 10 is first placed in the chamber 23 which has been removed from the hollow cylinder 20 and is then attached to the hollow cylinder 20 at one end thereof through the packing 24. Subsequently, the air in the apparatus A is removed by means of the vacuum pump P to reduce the pressure to a predetermined level. As a result, the treating chamber 23 is tightly sealed by the action of the differential pressure between the atmospheric pressure and the internal reduced pressure. Next, an inert gas such as argon is passed from the inlet 5 into the discharge chamber 1 so that the discharge chamber 1 is maintained at a pressure of 0.3 to 5 Torr. When the pair of capacitive electrodes are applied with a high frequency voltage from the high frequency power supply 8, the inert gas is ionized, thus generating a plasma. Part of the plasma is moved toward the treating chamber 23 by the action of the electrode 21 and irradiates the surface of the biological specimen 10 until the specimen 10 is activated with the ions of the inert gas by the atomic fabrication effect.

Figure 4:
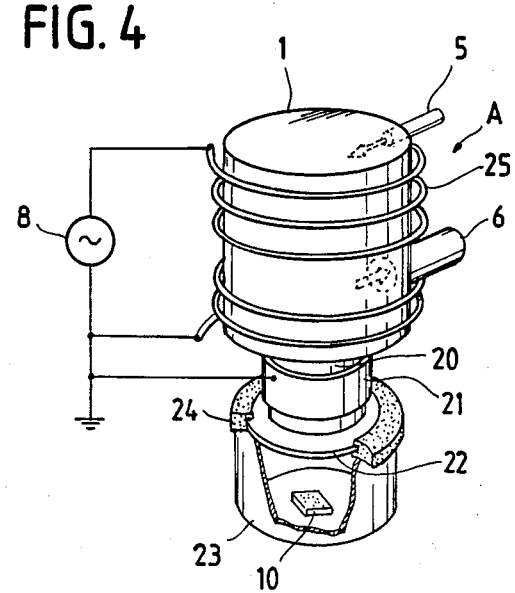
FIG. 4 is a perspective view similar to FIG. 3, showing a still further embodiment of the invention.

FIG. 4 shows another embodiment of the invention in which the pair of capacitive electrodes are replaced by an inductive coil electrode 25. The use of the inductive coil electrode 25 permits an inert gas to be ionized in a manner similar to the case of FIG. 3.

The method and apparatus of the present invention may be suitably applied to almost all biological materials without limitation.

The present invention is more particularly described by way of examples.

EXAMPLE 1

Figure 5:
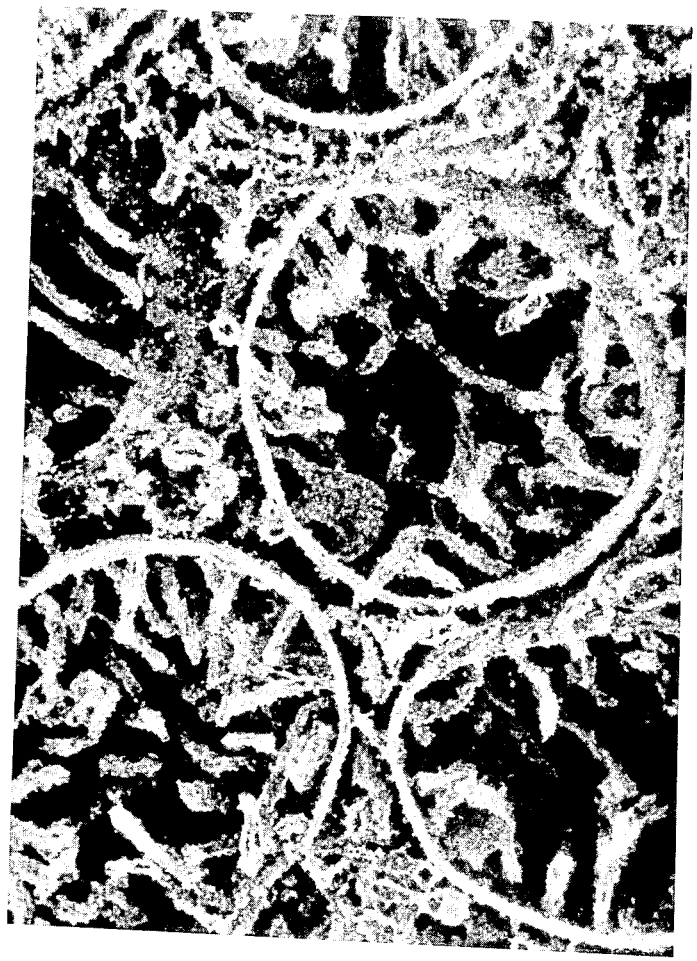
FIGS. 5 through 7 are microphotographs of biological materials treated according to the method of the invention.

The liver tissue of a rat was pretreated in an apparatus of the type shown in FIG. 1 under conditions of a vacuum of 2 to 1 Torr., a high frequency output power of 3 to 5 W and a treating time of 10 minutes. The thus treated tissue was observed through a scanning electron microscope, HFS-2 made by Hitachi Ltd. The resulting microphotograph ($\times 62,000$ magnifications) is shown in FIG. 5, revealing that the fine structure of mitochondoria of the liver cells is clearly shown.

EXAMPLE 2

Figure 6:
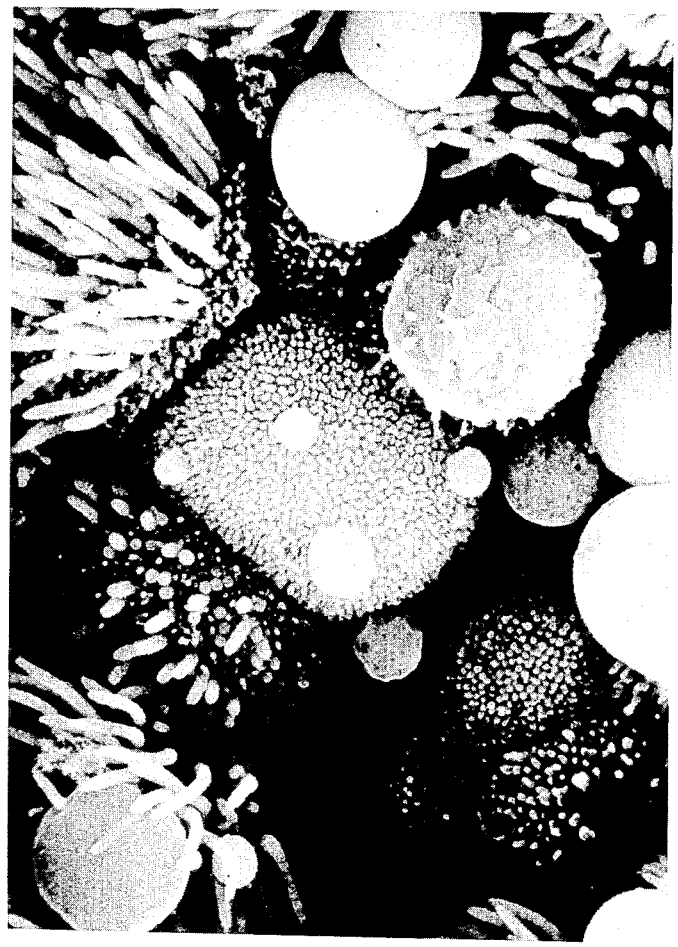
Figure 7:
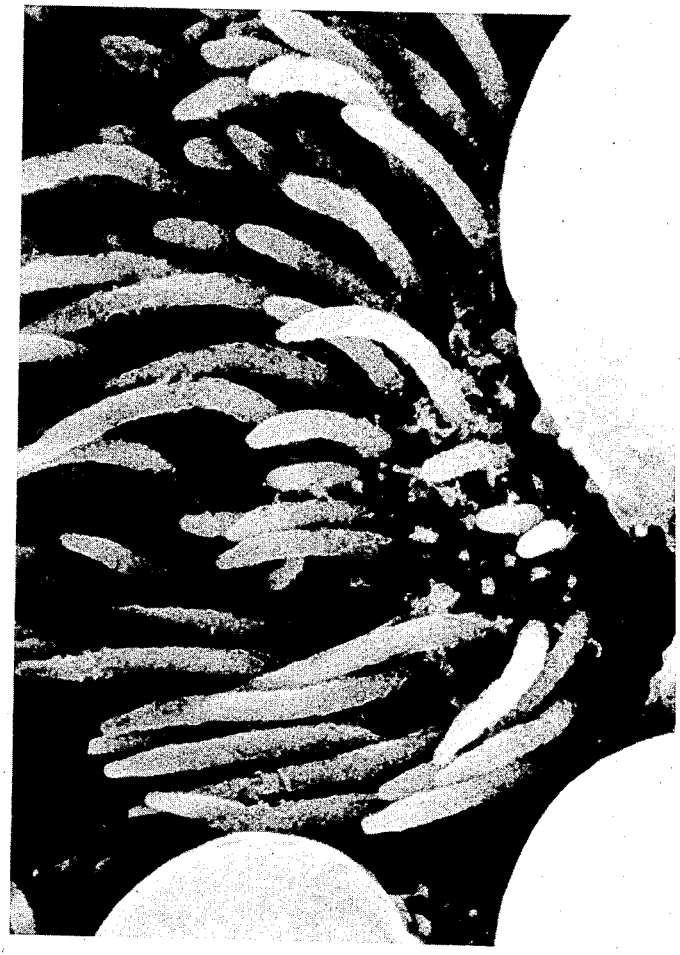

Epithelial cells of the tracheal mucosa of a rat were pretreated by an apparatus of the type shown in FIG. 3 under conditions of a vacuum of 2 to 1 Torr., a high frequency output power of 3 to 5 W and a treating time of 10 minutes. The resultant cells were observed through a scanning electron microscope as used in Example 1. The microphotographs ($\times 6700$ and $\times 12500$ magnifications) are shown in FIGS. 6 and 7, respectively. From these, it will be seen that fine structures of the cells are clearly observed.

We wish it to be understood that the invention is not to be limited to the specific constructions and arrangements shown and described, except only insofar as the claims may be so limited, as it will be understood to one skilled in the art that changes and variations may be made without departing from the principles of the invention.

What is claimed is:

1. A method for pretreating a biological material in a vacuum chamber for subsequent observation through a scanning electron microscope, the method comprising supplying only an inert gas to a vacuum chamber to provide a pressure within the vacuum chamber of from 0.3 to 5 Torr., energizing said inert gas by application of a high frequency output power of from 5 to 20 W for a period of from 5 to 10 minutes to generate inert gas ions and irradiating the surfaces of a biological material with said inert gas ions, whereby if the treated surfaces are subsequently irradiated with an electron beam for microscopic observation, secondary electrons are emitted from the treated surfaces.

2. A method according to claim 1, wherein said inert gas is argon.

3. A method according to claim 1, wherein said inert gas is energized in a first zone distant from a second zone where the biological material is placed, and part of the resulting ions are induced toward the second zone whereby the influence of heat generated by the energizing step is minimized.

* * * * *